United States Patent [19]

Kieczykowski

[11] Patent Number: 5,159,108
[45] Date of Patent: Oct. 27, 1992

[54] PROCESS FOR PREPARING AN ANTIHYPERCALCEMIC AGENT

[75] Inventor: Gerard R. Kieczykowski, Westfield, N.J.

[73] Assignee: Merck & Co., Inc., Rahway, N.J.

[21] Appl. No.: 742,142

[22] Filed: Aug. 1, 1991

Related U.S. Application Data

[63] Continuation of Ser. No. 584,318, Sep. 18, 1990, abandoned.

[51] Int. Cl.$^5$ .............................................. C07F 9/38
[52] U.S. Cl. ...................................... 562/13; 548/415
[58] Field of Search ........................... 562/13; 548/415

[56] References Cited

U.S. PATENT DOCUMENTS

| | | | |
|---|---|---|---|
| 4,407,761 | 10/1983 | Blum et al. | 260/502.5 C |
| 4,922,007 | 5/1990 | Kieczykowski et al. | 562/13 |
| 5,036,058 | 7/1991 | Jaeggi | 562/13 |
| 5,039,819 | 8/1991 | Kieczykowski | 548/415 |
| 5,110,807 | 5/1992 | Jaeggi | 562/13 |

OTHER PUBLICATIONS

J. Org. Chem., vol. 36, No. 24, 1971, pp. 3843–3845.
J. Am. Chem. Soc., vol. 70. Apr. 1948, pp. 1473–1474.
Chemistry of the Amino Acids, vol. 2 by J. P. Greenstein and M. Winitz, John Wiley, New York, pp. 901–907, 1280–1285 (1961).
J. Med. Chem., 1979, vol. 22, No. 11, pp. 1399–1402.
J. Am. Chem. Soc., vol. 74, pp. 3822–3825. (1952).
"The Peptides", vol. 3, by E. Gross and J. Meienhofer., 1981. pp. 9–10.
J. Med. Chem., 1987, vol. 30, pp. 1426–1433.
Eli Breuer, et al., *Novel Amino Acid Derivatives. Preparation and Properties of Aminoacylphosphonates and Amino Hydroxyimino Phosphonates*, J. Org. Chem. 1990, 55, 6147–6153.

*Primary Examiner*—Jose G. Dees
*Assistant Examiner*—B. Frazier
*Attorney, Agent, or Firm*—Robert J. North; Charles C. Caruso

[57] ABSTRACT

Described is a new process for producing 4-amino-1-hydroxybutylidene-1,1-bisphosphonic acid (ABP), a new antihypercalcemic agent. The process involves a 3-step sequence starting with 4-phthalimidobutanoyl chloride which can be practiced as a "one-pot" reaction sequence, without employing $PCl_3$ or $H_3PO_3$.

10 Claims, No Drawings

PROCESS FOR PREPARING AN ANTIHYPERCALCEMIC AGENT

This is a continuation of application Ser. No. 07/584,318, filed on Sep. 18, 1990 now abandoned.

BACKGROUND OF THE INVENTION

4-Amino-1-hydroxybutylidene-1,1-bisphosphonic acid (ABP), and salts thereof, is a new antihypercalcemic agent effective in the treatment or prevention of diseases involving hypercalcemia of pregnancy, Paget's disease and osteoporosis.

Methods for preparing ABP are known in the art and are disclosed in U.S. Pat. No. 4,407,761 to Henkel and U.S. Pat. No. 4,922,007 to G. R. Kiecykowski et al (assigned to Merck & Co., Inc.). However, these methods employ the use of toxic and environmentally dangerous phosphorus trichloride and phosphorous acid in their procedures. Newer methods which do not employ these particularly hazardous and toxic reagents are constantly being searched for.

The articles, *J. Org. Chem.* Vol. 36, No. 24, pp. 3843–45 (1971) and *J. Med. Chem.* 1987, Vol. 30, pp. 1426–1433, describe general methods of preparation of tetramethylalkyl-1-hydroxy-1,1-diphosphonates but do not specifically describe the preparation of omega-amino-1-hydroxyalkyl diphosphonates.

The use of the phthaloyl protecting group in amino acid chemistry is well known, e.g., *J. Med. Chem.* 1979, vol. 22, No. 11, pp. 1399–1402, but there is no specific teaching as to their possible use in preparing omega-amino-1-hydroalkyl diphosphonates.

SUMMARY OF THE INVENTION

It has been found that ABP can be produced in good yield via a novel process that does not employ $PCl_3$ or $H_3PO_3$. The process involves reacting 4-phthalimidobutanoyl chloride with a tri $C_1$-$C_4$ alkylphosphite, e.g., trimethyl phosphite, and then with a di $C_1$-$C_4$ alkylphosphite, e.g., dimethyl phosphite, to form the tetraalkyl ester, e.g., tetramethyl bisphosphonate, which is then acid hydrolyzed to form ABP in good yield and purity.

In addition, the process is applicable to the preparation of other omega-amino-1-hydroxy-$C_2$-$C_6$ alkyl disphosphonates as well.

By this invention there is provided a process for producing omega-amino-1-hydroxy-$C_2$-$C_6$ alkylidene-bisphosphonic acid comprising the steps of:

(a) contacting omega-phthalimido $C_2$-$C_6$ alkanoyl chloride with a tri $C_1$-$C_4$ alkyl phosphite in a dry inert organic solvent at a temperature in the range of 0° to 60° C. to form di $C_1$-$C_4$ alkyl omega-phthalimido-$C_2$-$C_6$ alkanoyl phosphonate;

(b) contacting di $C_1$-$C_4$ alkyl omega-phthalimido-$C_2$-$C_6$ alkanoyl phosphonate from Step (a) with di $C_1$-$C_4$ alkyl phosphite in a dry inert organic solvent in the temperature range of 0° to 60° C. to form tetra $C_1$-$C_4$ alkyl omega-phthalimido-1-hydroxy-$C_2$-$C_6$ alkylidene-bisphosphonate;

(c) contacting tetra $C_1$-$C_4$ alkyl omega-phthalimido-1-hydroxy-$C_2$-$C_6$ alkylidene-bisphosphonate from Step (b) with aqueous strong acid at a temperature in the range of 90° C. to reflux to form omega-amino-1-hydroxy-$C_2$-$C_6$ alkylidene-bisphosphonic acid.

Specifically there is provided a process for producing 4-amino-1-hydroxybutylidene-bisphosphonic acid comprising the steps of:

(a) contacting 4-phthalimidobutanoyl chloride with trimethyl phosphite in a dry inert organic solvent at a temperature in the range of 0° to 60° C. to form dimethyl 4-phthalimidobutanoyl phosphonate;

(b) contacting dimethyl 4-phthalimidobutanoyl phosphonate from Step (a) with dimethyl phosphite in a dry inert organic solvent in the temperature range of 0° to 60° C. to form tetramethyl phthalimido-1-hydroxy butylidene-bisphosphonate;

(c) contacting tetramethyl phthalimido-1-hydroxybutylidene-bisphosphonate from Step (b) with aqueous hydrochloric acid at a temperature range of 80° C. to reflux to form 4-amino-1-hydroxybutylidene-bisphosphonic acid.

BRIEF DESCRIPTION OF PREFERRED EMBODIMENTS

The invention process can be more readily seen and appreciated by referring to the following Flow Chart 1. This new process for the preparation of ABP can proceed in good overall yield from gamma-4-aminobutyric acid (GABA). As depicted in the flow chart, phthalic anhydride is reacted with GABA, e.g. in acetic acid, to form the known 4-phthalimidobutyric acid 1 which can be isolated by e.g., crystallization from acetic acid-water. It is converted into the known acid chloride 2 by reaction with about 1.2 equivalents of thionyl chloride in, e.g. toluene, and without isolation can be converted to the acyl phosphonate 3 with about 1.05 equivalents of trimethyl phosphite. The acyl phosphonate 3 can then be in turn converted, without isolation, into the bisphosphonate 4 by reacting with dimethyl phosphite (in e.g. toluene) in the presence of an amine base, e.g., triethylamine. The bisphosphonate can crystallize as it is formed and can be isolated by filtration in good overall yield. Hydrolysis of the bisphosphonate with a strong aqueous acid, e.g., 6N HCl, provides ABP which can then be converted into the monosodium salt, which is the preferred pharmaceutical dosage form, with sodium hydroxide at about a pH of 4.3, in which the sodium aqueous salt can easily be isolated.

In addition to utilizing 4-aminobutanoic acid, also operable are glycine, 3-aminopropanoic acid, 5-aminopentanoic acid and 6-aminohexanoic acid, which yield the corresponding omega-amino-1-hydroxy $C_2$-$C_6$ alkylbisphosphonates in the invention process, e.g., 2-amino-1-hydroxyethylidene-1,1-bisphosphonic acid, 3-amino-1-hydroxypropylidene-1,1-bisphosphonic acid, 5-amino-1-hydroxypentylidene-1,1-bisphosphonic acid, 6-amino-1-hydroxy-hexylidene-1,1-bisphosphonic acid.

More detail concerning the individual steps is as follows:

FLOW CHART

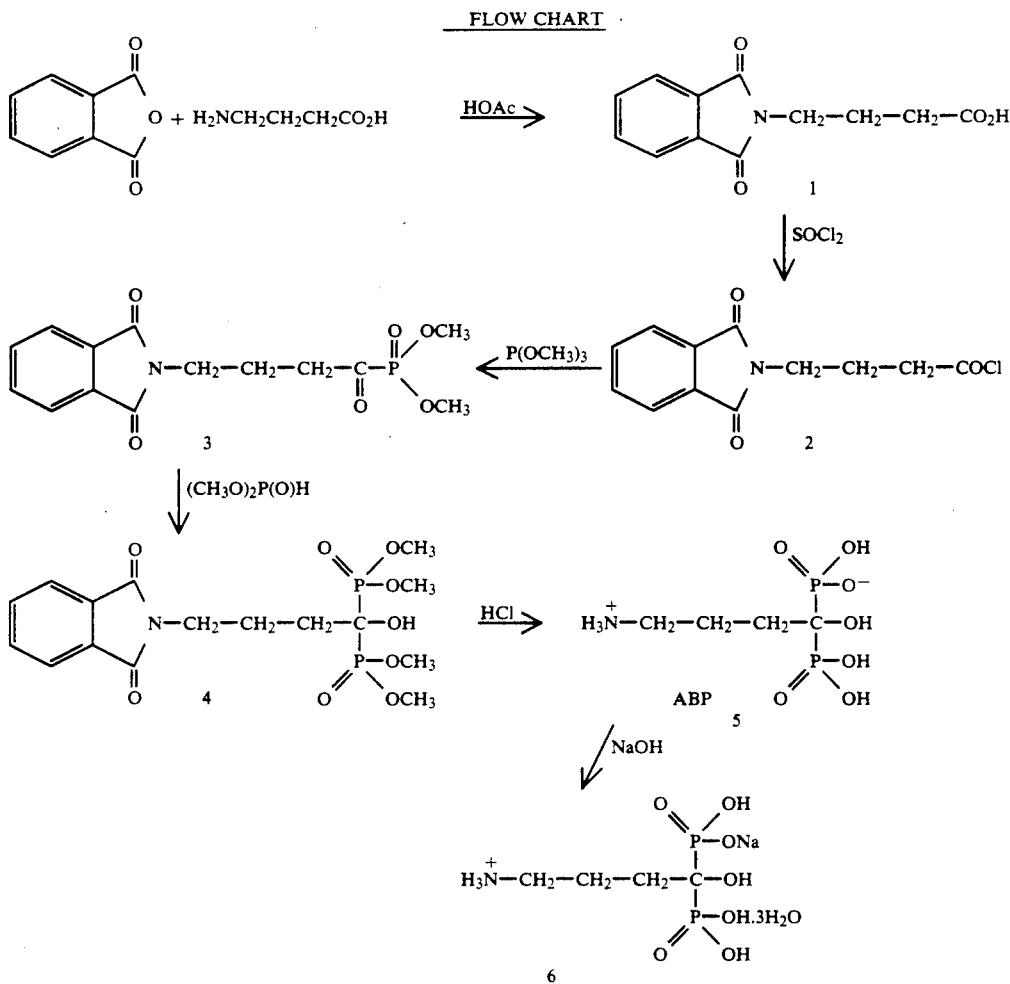

The 4-phthalimidobutanoic acid is known in the art. The compound can be easily made in our process by for example, reacting phthalic anhydride and aqueous aminobutyric acid in a 1:1 mole ratio in a liquid alkanoic acid, e.g. acetic acid, at about a 40% concentration, at a temperature in the range of 60° to reflux, preferably 110° C., for about 1-4 hours at 1 atmosphere pressure, under anhydrous conditions and then quenching the reaction mixture with water to isolate the resulting acid (1).

The acid chloride (2) also known in the art can easily be made by heating a mixture of the acid (1) with thionyl chloride in a 1:1.2 molar ratio in a dry inert solvent, including $C_6$-$C_{10}$ aromatic hydrocarbons, chlorinated $C_6$-$C_{10}$ aromatic hydrocarbons, chlorinated alkyl hydrocarbons, $C_2$-$C_3$ alkylnitriles, $C_4$-$C_6$ linear or cyclic ethers. Representative examples are: toluene, xylene, methylene chloride, chloroform, chlorobenzene, acetonitrile, ethylene dichloride, dichlorobenzene, THF, dioxane, dimethoxyethane, and the like, at a temperature of about 40° C.-reflux, preferably 45° C., at atmospheric pressure, under a dry atmosphere, e.g. under nitrogen, for 1-2 hours. The resulting acid chloride does not need to be isolated at this point but can be used directly in the next step by evaporating off the excess thionyl chloride and concentrating the solvent toluene to about one-half its original volume.

Step (a) in the process is conducted by reacting the acid chloride (2) with a tri $C_1$-$C_4$ alkylphosphite, wherein $C_1$-$C_4$ alkyl includes methyl, ethyl, propyl, isopropyl, n-butyl, isobutyl, sec-butyl t-butyl, e.g., trimethyl phosphite. In general, a 1:1.05 molar ratio of acid chloride/trimethylphosphite is used, in which a slight excess of phosphite is employed. The solvent used can be the same as that described above used in forming the acid chloride, e.g. toluene, et al., and preferably the same reaction vessel is employed. The concentration of the reactants is about 5-50% and the reaction is carried out at a temperature of 0°-60° C., preferably 20°-25° C., in the solvent in a dry atmosphere, e.g. under nitrogen, for 4-20 hours at atmospheric pressure. The resulting mono-phosphonate (3) does not need to be isolated but can be directly reacted without isolation with dimethylphosphite in Step (b).

The acylphosphonate (3) is next reacted in Step (b) with or without prior isolation, preferably without isolation, with a di $C_1$-$C_4$ alkyl phosphite, wherein "$C_1$-$C_4$ alkyl" is defined above, and preferably dimethylphosphite, in a 1:1.1 molar ratio, the dimethylphosphite being in slight excess, also in the presence of a hydrogen acceptor, e.g. tertiary nitrogen amine. Large amounts of the phosphite can also be used but are not necessary. The amine, preferably a tertiary nitrogen amine, e.g. trimethylamine, triethylamine, phenyldimethylamine, and the like, is used in a 0.25-1:1 molar ratio of amine/acylphosphonate (3). The inert solvent used in this step can be the same as used for Step (a), e.g. toluene, methylene chloride, chloroform, and the like, preferably toluene. The temperature for the step is carried out at 0°-60° C., preferably 20°-25° C., wherein higher temperatures may cause degradation. The pressure is atmospheric, and the reaction is conducted under a dry atmosphere, e.g. nitrogen, for 1-2 hours and then cooled and filtered to isolate the product. Alternatively, the product can be directly treated in Step (c) with aqueous strong acid in the hydrolysis, but preferably for purity consideration, at this point, the tetramethyl ester (4) is isolated by filtration.

Step (c), the strong acid hydrolysis, is conducted by treating the bisphosphonate (4) with aqueous strong acid at a temperature in the range of 85°-100° C. to reflux, and preferably at reflux. Strong acids operable in the process are: HCl, H₂SO₄, benzenesulfonic acid, p-toluenesulfonic acid, methanesulfonic acid, HBr, trichloroacetic acid, and the like. Preferably, 6N HCl is used. Generally the reaction is conducted from 4-24 hours at reflux at atmospheric pressure. The product can be isolated by the addition of e.g. ethanol, to precipitate the product and the solution. Or preferably, the monosodium salt can be formed in-situ by the addition of aqueous sodium hydroxide to the cooled hydrolysis reaction mixture, sufficient caustic being added to dissolve the acid and produce a pH of about 4.3, allowing the reaction mixture to age for 1 hour, then filtering the monosodium salt. The obtained salt can be used directly or purified by conventional purposes, e.g. recrystallization from water to form suitable material for pharmaceutical purposes.

Apparatus for carrying out the above procedures is conventional in the art.

Also disclosed is the novel general process intermediate compound (III)

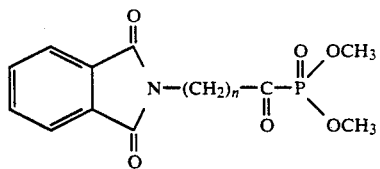

where n=1-5, and the specific intermediate (3),

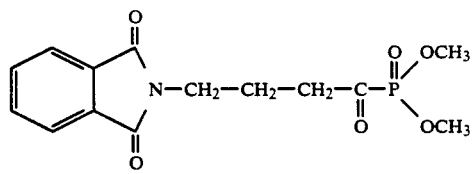

made by the above process and having the following physical properties described below in the Examples.

Also disclosed is the novel general process intermediate compound (IV)

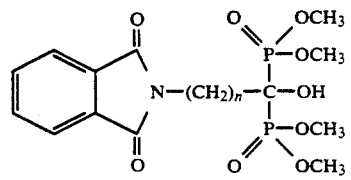

where n=1-5, and the specific intermediate (4):

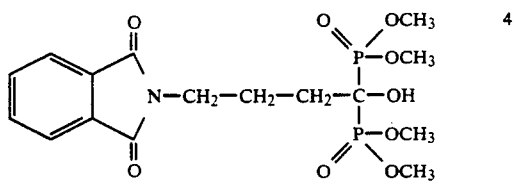

made by the above process and having the above physical properties described below in the Examples.

The following Examples are illustrative of carrying out Applicant's novel process and should not be construed to limit the scope or spirit of Applicant's invention.

EXAMPLE

Step 1

Preparation of 4-Phthalimidobutanoic Acid (1)

A 2 liter nitrogen flushed flask fitted with a mechanical stirrer and a reflux condenser was charged with 103 g (1 mole) of 4-aminobutyric acid (GABA), 148 g (1 mole) of phthalic anhydride and 250 ml of glacial acetic acid.

The suspension was heated to reflux (120° C.) and the resulting clear solution was maintained at reflux for 2 hr. The solution was cooled to 25° C. over 1 hr during which time the product crystallized out. Water (1.5 liters) was added over 15 min. and the resulting suspension aged at 5°-10° C. for 2 hours. The product was collected by filtration and washed with an additional 0.5 l of water. The product was vacuum dried (house vac) at 60° C. to constant weight yielding 214 g (91.8%, 93% corrected for GABA purity), MP 114°-117° C.

Anal. Calcd. For $C_{12}H_{11}NO$: C, 61.80; H, 4.72; N, 6.00; Found: C, 61.78; H, 4.65; N, 5.98.

Step 2

Preparation of 4-Phthalimidobutanoyl Chloride (2)

A 250 ml flask flushed and blanketed with nitrogen and fitted with a mechanical stirrer was charged with 23.3 g of 4-phthalimidobutyric acid from Step 1, 100 ml of toluene, 9.0 ml of thionyl chloride and 0.1 ml of DMF. The slurry was agitated gently and warmed to 45°-50° C. resulting in a clear, colorless solution.

During the age, gentle gas evolution was observed and ceased approximately 1 hour into the age. The excess thionyl chloride was removed by distillation. The volume of the reaction was reduced to 50 ml by distillation under house vacuum (100 mm Hg) and a jacket temperature of 80° C. An additional 100 ml of toluene was added and distilled. The clear, colorless solution was used without purification.

The acid chloride was isolated for characterization as a crystalline solid by concentrating the solution to an oil, adding diethyl ether and filtering, MP 65°-68° C.

Anal. Calcd. For $C_{12}H_{10}NO_3Cl$: C, 57.26; H, 3.97; N, 5.56; Cl, 14.09; Found: C, 57.48; H, 4.07; N, 5.52; Cl, 14.05.

Step 3

Preparation of Dimethyl 4-Phthalimidobutanoyl Phosphonate (3)

The toluene solution from Step 2 containing a theoretical 25.1 g (0.1 mole) of acid chloride was stirred at 20°-25° C. under nitrogen. To this solution was charged 13.0 g (0.105 mole) of trimethyl phosphite in one portion. The reaction temperature increased slightly from 25° C. to 27° C. The clear colorless solution was aged at 20°-25° C. for 18 hours.

Once the formation of the acyl phosphonate was complete, the solution was used without purification for the next reaction in the sequence, formation of the tetraalkyl bisphophonate ester. The acyl phosphonate was isolated as a crystalline solid by concentrating in vacuo to almost dryness, adding hexanes and filtering, MP 60°-63° C.

Anal. Calcd. For $C_{14}H_{16}NO_6P$: C, 51.69; H, 4.92; N, 4.30; P, 9.53; Found: C, 51.27; H, 4.93; N, 4.25; P, 9.31.

Step 4

Preparation of Tetramethyl Phthalimido-1-Hydroxybutylidene)Bisphosphonate (4)

The toluene solution from Step 3 containing a theoretical 32.5 g (0.1 mole) of the acyl phosphonate was used without purification for formation of the tetraalkyl bisphophonate ester. To the solution stirred at 20°-25° C. under nitrogen was added dimethyl phosphite, 11.6 g (0.105 mole) in one portion. Triethylamine, 10.0 g (0.1 mole) was added dropwise over 15 minutes while maintaining a reaction temperature of 20°-25° C. with external cooling. During the addition of the triethylamine there was a rapid crystallization of the bisphosphonate resulting in a thick slurry. The slurry was stirred at 20°-25° C. for an additional 1 hour.

The reaction mixture was cooled to 0°-5° C., aged for 1 hour then filtered. The cake was washed with 50 ml of toluene and the product dried in vacuo (house vacuum) at 40° C. to constant weight yielding 40.0 g (92%) of white crystalline bisphosphonate, MP 140°-143° C.

Anal. Calcd. For $C_{16}H_{23}NO_9P_2$: C, 44.14; H, 5.28; N, 3.21; P, 14.24; Found: C, 44.10; H, 5.23; N, 3.09; P, 14.20.

Step 5

Preparation of (4-Amino-1-Hydroxybutylidene)Bisphosphonic Acid (ABP) (5)

Tetramethyl-1,1-bisphosphono-1-hydroxy-4-phthalimidobutane 40 g (0.091 mole) from Step 4 was dissolved in 200 ml of 6N HCl and the solution refluxed for 18 hours.

The resulting suspension was cooled to 0°-5° C. and the phthalic acid was removed by filtration. The phthalic acid cake was washed with 50 ml of 6N HCl and the combined filtrate concentrated to 25 ml then flushed with an additional 50 ml of water. The solution was cooled to 20°-25° C. during which time the ABP crystallizes. The crystallization was completed by adding 75 ml of 95% ethanol.

The suspension was cooled to 0°-5° C. and aged at that temperature for 2 hours. The titled product was collected by filtration and washed with 25 ml of 95% ethanol. The yield was 24.0 g (97.8%, but 89.8% based on starting GABA) after air drying to constant weight.

Step 6

Preparation of (4-Amino-1-Hydroxybutylidene)-Bisphosphonic Acid Monosodium Salt Trihydrate (6)

Ten grams (37.4 mmol) of (4-amino-1-hydroxybutylidene)biphosphonic acid, (ABP) was suspended in 300 mL of distilled deionized water with vigorous stirring at 25° C. The pH was 2.27 and was titrated to pH 4.3 to 4.4 by the gradual addition of 7.5 ml (37.4 mmol) 5N sodium hydroxide solution, resulting in a clear solution.

The clear solution was filtered through a medium sintered-glass funnel to remove any insoluble material. Twenty percent of the filtrate (~60 mL) was addedover 5 minutes to 400 mL of 95% ethanol at 20°-25° C. with vigorus stirring and aged for one hour.

The remaining 240 mL of aqueous solution was added over 15 minutes and the mixture aged for 2 hours at 20°-25° C. The white sodium salt was collected by filtration, washed with 100 ml of 2:1 EtOH:H₂O and air dried at 40° C. to yield 11.25 g (93%) of mono sodium salt trihydrate.

What is claimed is:

1. A process for producing omega-amino-1-hydroxy-$C_2$-$C_6$-alkylidene-bisphosphonic acid comprising the steps of:

(a) contacting omega-phthalimido-$C_2$-$C_6$ alkanoyl chloride with tri $C_1$-$C_4$ alkyl phosphite in a dry inert organic solvent at a temperature in the range of 0° to 60° C. to form di $C_1$-$C_4$ alkyl omega-phthalimido-$C_2$-$C_6$-alkanoyl phosphonate;

(b) contacting di $C_1$-$C_4$ alkyl omega-phthalimido-$C_2$-$C_6$-alkanoyl phosphonate from Step (a) with di $C_1$-$C_4$ alkyl phosphite in a dry inert organic solvent in the temperature range of 0° to 60° C. in the presence of a tertiary nitrogen amine, to form tetra $C_1$-$C_4$ alkyl omega-phthalimido-1-hydroxy-$C_2$-$C_6$-alkylidene-bisphosphonate;

(c) contacting tetra $C_1$-$C_4$ alkyl omega-phthalimido-1-hydroxy-$C_2$-$C_6$-alkylidene-bisphosphonate from Step (b) with aqueous strong acid at a temperature in the range of 90° C. to reflux to form omega-amino-1-hydroxy-$C_2$-$C_6$-alkylidene-bisphosphonic acid.

2. The process of claim 1 wherein said alkanoyl chloride is derived from glycine, 3-aminopropanoic acid, 4-aminobutanoic acid, 5-aminopentanoic acid or 6-aminohexanoic acid.

3. The process of claim 1 wherein the temperature range for Step (a) is in the range of 20° to 25° C.

4. The process of claim 1 wherein the temperature range for Step (b) is in the range of 20° to 25° C.

5. The process of claim 1 wherein the temperature for Step (c) is the reflux temperature of the solvent.

6. The process of claim 1 wherein the solvent for Step (a) is selected from $C_6$-$C_{10}$ aromatic hydrocarbons, chlorinated $C_6$-$C_{10}$ aromatic hydrocarbons, chlorinated $C_1$-$C_4$ alkyl hydrocarbons, $C_2$-$C_3$ alkylnitriles, $C_4$-$C_6$ linear or cyclic ethers.

7. The process of claim 1 wherein the solvent for Step (b) is the same as for Step (a).

8. The process of claim 1 wherein the strong acid in Step (c) is aqueous hydrochloric acid.

9. The process of claim 1 wherein the product phosphonate from Step (a) is not isolated prior to conducting Step (b).

10. A process for producing 4-amino-1-hydroxybutylidene-bisphosphonic acid comprising the steps of:

(a) contacting 4-phthalimidobutanoyl chloride with trimethyl phosphite in a dry inert organic solvent at a temperature in the range of 0° to 60° C. to form dimethyl 4-phthalimidobutanoyl phosphonate;

(b) contacting dimethyl 4-phthalimidobutanoyl phosphonate from Step (a) with dimethylphosphite in a dry inert organic solvent in the temperature range of 0° to 60° C. to form tetramethyl phthalimido-1-hydroxybutylidene-bisphosphonate;

(c) contacting tetramethyl phthalimido-1-hydroxybutylidene-bisphosphonate from Step (b) with aqueous hydrochloric acid at a temperature in the range of 80° C. to reflux to form 4-amino-1-hydroxybutylidene-bisphosphonic acid.

* * * * *